(12) United States Patent
Yoon

(10) Patent No.: US 10,815,442 B2
(45) Date of Patent: Oct. 27, 2020

(54) APPARATUS AND PROCESS FOR SYNTHESIZING NATURAL GAS USING CARBON DIOXIDE AND WATER IN AIR

(71) Applicant: Sogang University Research & Business Development Foundation, Mapo-gu, Seoul (KR)

(72) Inventor: Kyung Byung Yoon, Seoul (KR)

(73) Assignee: Sogang University Research & Business Development Foundation, Mapo-Gu, Seoul (KR)

( * ) Notice: Subject to any disclaimer, the term of this patent is extended or adjusted under 35 U.S.C. 154(b) by 0 days.

(21) Appl. No.: 16/460,071

(22) Filed: Jul. 2, 2019

(65) Prior Publication Data

US 2020/0010771 A1    Jan. 9, 2020

(30) Foreign Application Priority Data

Jul. 2, 2018 (KR) .................. 10-2018-0076297

(51) Int. Cl.
*C10L 3/08* (2006.01)
*B01D 53/22* (2006.01)
(Continued)

(52) U.S. Cl.
CPC .............. *C10L 3/08* (2013.01); *B01D 53/02* (2013.01); *B01D 53/229* (2013.01);
(Continued)

(58) Field of Classification Search
CPC ........ B01D 53/00; B01D 53/02; B01D 53/22; B01D 53/229; B01D 53/26; B01D 53/261; B01D 53/265; B01D 53/268; B01D 2253/00; B01D 2253/10; B01D 2253/106; B01D 2253/108; B01D 2253/20; B01D 2253/204; B01D 2257/00; B01D 2257/50; B01D 2257/504; B01D 2257/80; B01J 19/00; B01J 19/0006; B01J 19/0013; B01J 19/08; B01J 2219/00; B01J 2219/00049;
(Continued)

(56) References Cited

FOREIGN PATENT DOCUMENTS

FR    3074971 A1 *  6/2019  ............. C25B 9/206
JP    2017057491 A    3/2017
(Continued)

*Primary Examiner* — Natasha E Young
(74) *Attorney, Agent, or Firm* — Hamre, Schumann, Mueller & Larson, P.C.

(57) ABSTRACT

An apparatus for producing a natural gas using carbon dioxide and water in air that includes an air-compressing member, a water collecting member, a water storing member, a carbon dioxide collecting member, a water electrolysis member, and a methanation reaction member. The water electrolysis member electrolyzes water separated from compressed air. The methanation reaction member generates a natural gas by reacting hydrogen from the electrolysis and carbon dioxide from the carbon dioxide collecting member. A method of producing a natural gas using carbon dioxide and water in air includes supplying hydrogen electrolyzed from water separated from air and carbon dioxide collected from the dry air to a methanation reaction member to generate a natural gas. A natural gas-synthesizing equipment system includes an apparatus for producing a natural gas using carbon dioxide and water in air.

14 Claims, 2 Drawing Sheets

(51) Int. Cl.
*B01D 53/26* (2006.01)
*B01J 19/00* (2006.01)
*B01J 19/24* (2006.01)
*C07C 1/04* (2006.01)
*C25B 1/04* (2006.01)
*F25J 3/04* (2006.01)
*B01D 53/02* (2006.01)
*B01J 19/08* (2006.01)

(52) U.S. Cl.
CPC ......... *B01D 53/261* (2013.01); *B01D 53/265* (2013.01); *B01D 53/268* (2013.01); *B01J 19/0013* (2013.01); *B01J 19/08* (2013.01); *C07C 1/041* (2013.01); *C07C 1/0485* (2013.01); *C25B 1/04* (2013.01); *F25J 3/04018* (2013.01); *B01D 2253/108* (2013.01); *B01D 2253/204* (2013.01); *B01D 2257/504* (2013.01); *B01D 2257/80* (2013.01); *B01J 2219/00164* (2013.01); *B01J 2219/0875* (2013.01); *B01J 2219/0898* (2013.01); *C10L 2200/0492* (2013.01); *C10L 2290/42* (2013.01)

(58) Field of Classification Search
CPC .......... B01J 2219/00164; B01J 2219/08; B01J 2219/0873; B01J 2219/0875; B01J 2219/0894; B01J 2219/0898; C07C 1/00; C07C 1/02; C07C 1/04; C07C 1/0405; C07C 1/041; C07C 1/0485; C07C 1/12; C10L 3/00; C10L 3/06; C10L 3/08; C10L 2200/00; C10L 2200/04; C10L 2200/0461; C10L 2200/0469; C10L 2200/0492; C10L 2290/00; C10L 2290/42; C10L 2290/46; C25B 1/00; C25B 1/02; C25B 1/04; F25J 3/00; F25J 3/02; F25J 3/04; F25J 3/04006; F25J 3/04012; F25J 3/04018
See application file for complete search history.

(56) References Cited

FOREIGN PATENT DOCUMENTS

| | | | |
|---|---|---|---|
| KR | 101648976 B1 | 8/2016 | |
| KR | 10-20180030677 A | 3/2018 | |
| WO | WO-2014154250 A1 * | 10/2014 | ............... C07C 1/12 |

* cited by examiner

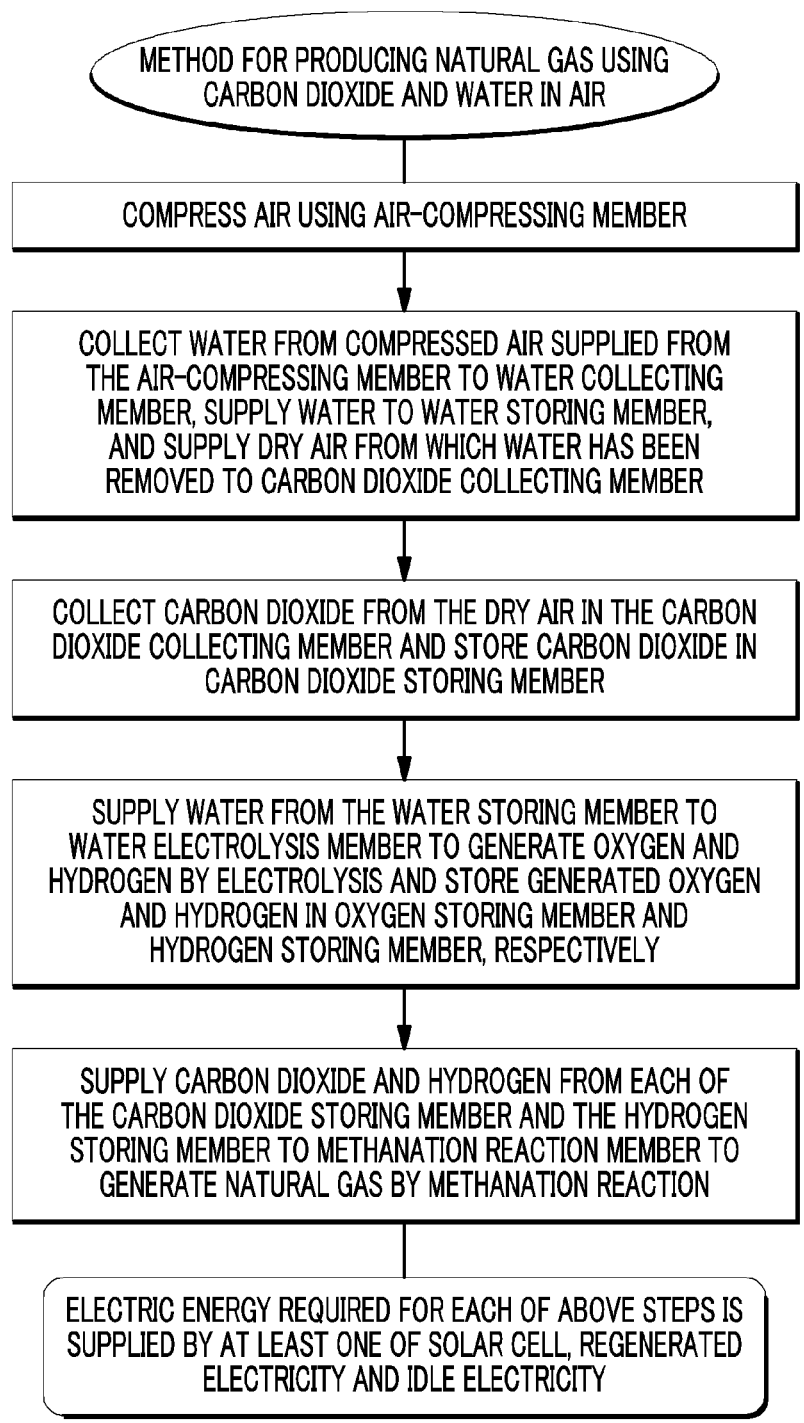

APPARATUS AND PROCESS FOR SYNTHESIZING NATURAL GAS USING CARBON DIOXIDE AND WATER IN AIR

CROSS-REFERENCE TO RELATED APPLICATION

This application Claims the benefit under 35 USC 119(a) of Korean Patent Application No. 10-2018-0076297 filed on Jul. 2, 2018 in the Korean Intellectual Property Office, the entire disclosure of which is incorporated herein by reference for all purposes.

TECHNICAL FIELD

The present disclosure relates to an apparatus for producing a natural gas using carbon dioxide and water in air, a method for producing a natural gas using carbon dioxide and water in air, and a natural gas-synthesizing equipment system including the apparatus. Particularly, the present disclosure relates to an apparatus and method for producing a natural gas with carbon dioxide and water collected from air by using electrical energy such as a solar cell, regenerated electricity, and idle electricity.

BACKGROUND

Today, the greenhouse effect caused by carbon dioxide ($CO_2$) emitted by the use of fossil fuels, such as coal, gasoline, and natural gas contributes to global warming and climate change and also results in global environmental problems that can have a huge impact on environment, society, and economy. In 2010, global $CO_2$ emission increased to 30.6 billion tons or more, and China became the largest $CO_2$ emission country and still produces an increasing amount of $CO_2$. People around the world suffer from shortages of energy and environmental problems caused by $CO_2$ emission are getting worse and worse. Therefore, methods for solving these problems have been researched.

As one of methods for reducing $CO_2$ emission, an efficient technique of converting $CO_2$ into a useful fuel material is being increasingly studied. However, such conversion requires electrical energy and fossil fuels are used for producing electrical energy, which results in a vicious circle of $CO_2$ emissions.

Accordingly, there has been demanded an efficient technique of converting $CO_2$ into a useful fuel material using renewable energy and idle electricity that require minimum electrical energy.

PRIOR ART DOCUMENT

Japanese Patent Laid-open Publication No. 10-2017-057491

SUMMARY

The present disclosure provides an apparatus for producing a natural gas using carbon dioxide and water in air, a method for producing a natural gas using carbon dioxide and water in air, and a natural gas-synthesizing equipment system including the apparatus. Particularly, the present disclosure relates to an apparatus for producing a natural gas with carbon dioxide and water collected from air by using electrical energy such as a solar cell, regenerated electricity, and idle electricity, a method for producing a natural gas using the apparatus, and a natural gas-synthesizing equipment system including the apparatus.

However, problems to be solved by the present disclosure are not limited to the above-described problems. Although not described herein, other problems to be solved by the present disclosure can be clearly understood by a person with ordinary skill in the art from the following descriptions.

A first aspect of the present disclosure provides a natural gas producing apparatus 100 using carbon dioxide and water in air, including the following: an air-compressing member 110; a water collecting member 120 for collecting and separating water from the compressed air supplied from the air-compressing member 110; a water storing member 130 connected to the water collecting member 120 and for storing the collected water; a carbon dioxide collecting member 140 connected to the water collecting member 120 and for collecting carbon dioxide from dry air supplied after the water collecting member 120 collects water; a water electrolysis member 150 for electrolyzing water supplied from the water storing member 130 to generate oxygen and hydrogen; a methanation reaction member 160 for generating a natural gas by methanation reaction of hydrogen supplied from a hydrogen storing member 153 connected to the water electrolysis member 150 and carbon dioxide supplied from a carbon dioxide storing member 141 connected to the carbon dioxide collecting member 140; a separation member 170 having a means for separating the natural gas, carbon dioxide and water contained in a methanation reaction product supplied from the methanation reaction member 160, respectively; a product storing member 180 for storing the natural gas supplied from the separation member 170, from which water and carbon dioxide are removed; and an oxygen storing member 158 for storing oxygen gas supplied from the water electrolysis member 150, wherein an electrical energy required for operating the apparatus is supplied by at least one of a solar cell, regenerated electricity, and idle electricity.

A second aspect of the present disclosure provides a method for producing a natural gas using carbon dioxide and water in air, including the following: compressing air using an air-compressing member; collecting water from the compressed air supplied from the air-compressing member to a water collecting member, supplying the water to a water storing member, and supplying dry air from which water has been removed to a carbon dioxide collecting member; collecting carbon dioxide from the dry air in the carbon dioxide collecting member and storing carbon dioxide in a carbon dioxide storing member; supplying water from the water storing member to a water electrolysis member to generate oxygen and hydrogen by electrolysis and storing the generated oxygen and hydrogen in an oxygen storing member and a hydrogen storing member, respectively; and supplying carbon dioxide and hydrogen from each of the carbon dioxide storing member and the hydrogen storing member to a methanation reaction member to generate a natural gas by a methanation reaction, wherein an electric energy required for each of the above steps is supplied by at least one of a solar cell, regenerated electricity and idle electricity.

A third aspect of the present disclosure provides a natural gas-synthesizing equipment system including the natural gas producing apparatus according to the first aspect of the present disclosure and a container including the apparatus.

By using an apparatus and method for producing a natural gas using carbon dioxide and water in air according to embodiments of the present disclosure, a natural gas containing a methane gas can be produced from carbon dioxide and water collected from air using an electric energy such as a solar cell, regenerated electricity and idle electricity. Particularly, in regions, such as deserts, with abundant solar energy but a lack of water, air in the deserts can be compressed to collect and separate water and dry air, respectively, hydrogen and oxygen can be generated by electrolysis of the collected water using an electric energy generated by a solar cell or solar power generation with abundant solar energy in the deserts, and carbon dioxide collected from the dry air and the hydrogen can be converted into a natural gas containing methane through a methanation reaction by using the apparatus and method for producing a natural gas according to embodiments of the present disclosure. Also, some of the collected water can be supplied as drinking water, agricultural water, and the like to the desert regions and the oxygen gas can be separately stored and supplied. The air is not limited as long as it contains carbon dioxide and water. For example, air in the atmosphere or emissions from various sources (for non-limiting example: emissions from factories, power plants, etc.) may be used as the air.

BRIEF DESCRIPTION OF THE DRAWINGS

In the detailed description that follows, embodiments are described as illustrations only since various changes and modifications will become apparent to a person with ordinary skill in the art from the following detailed description. The use of the same reference numbers in different figures indicates similar or identical items.

FIG. 2 is a flowchart showing a method for producing a natural gas using carbon dioxide and water in air in accordance with an embodiment of the present disclosure.

DETAILED DESCRIPTION

Figure 1:
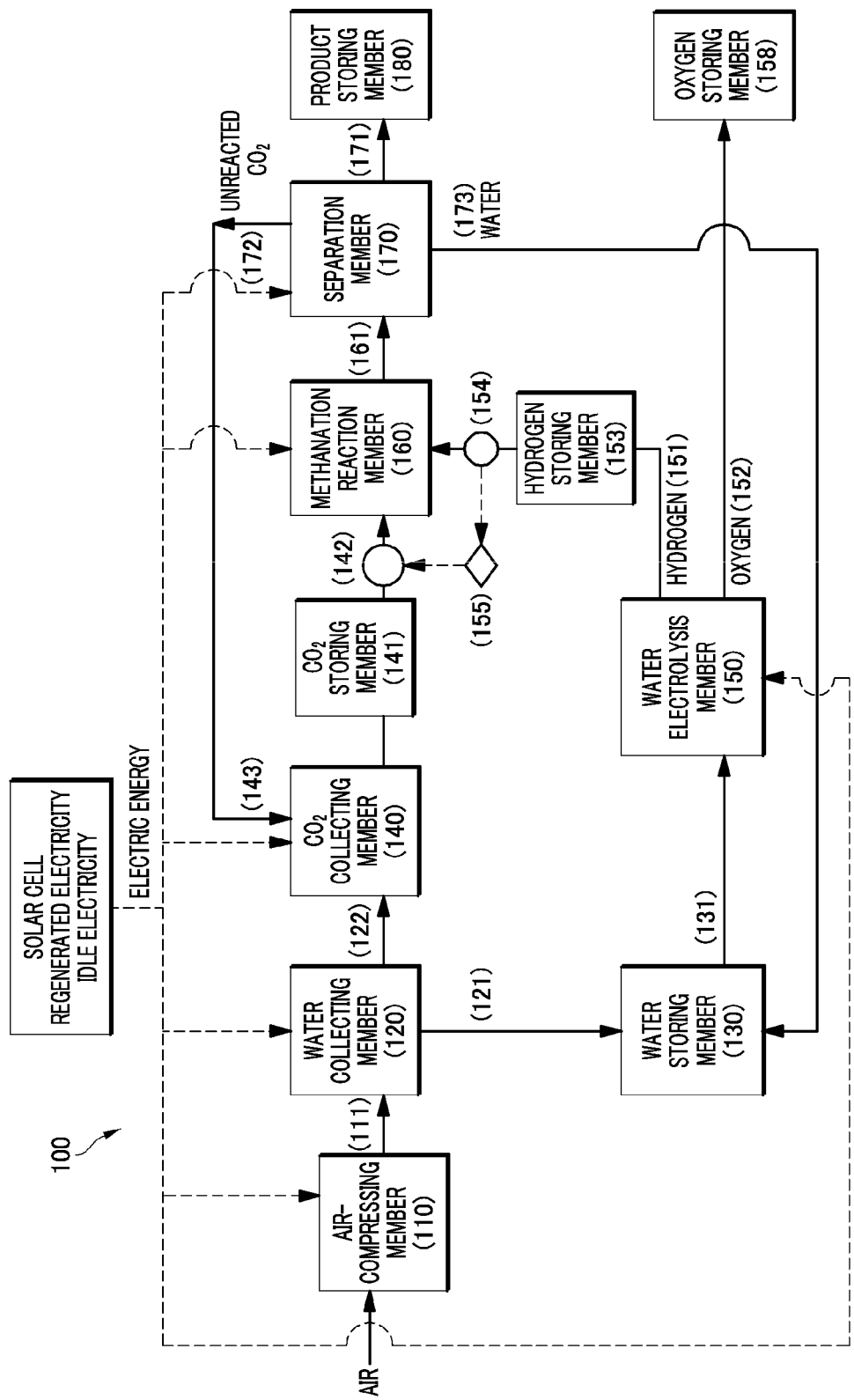
FIG. 1 is a schematic diagram illustrating an apparatus for producing a natural gas using carbon dioxide and water in air in accordance with an embodiment of the present disclosure.

Hereafter, examples will be described in detail with reference to the accompanying drawings so that the present disclosure may be readily implemented by a person with ordinary skill in the art. However, it is to be noted that the present disclosure is not limited to the examples but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected to" another element and an element being "electronically connected to" another element via another element.

Through the whole document, the term "on" that is used to designate a position of one element with respect to another element includes both a case that the one element is adjacent to the other element and a case that any other element exists between these two elements.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Hereafter, embodiments of the present disclosure will be described in detail with reference to the accompanying drawings, but the present disclosure may not be limited thereto.

A first aspect of the present disclosure relates to a natural gas producing apparatus 100 using carbon dioxide and water in air, including the following: an air-compressing member 110; a water collecting member 120 for collecting and separating water from the compressed air supplied from the air-compressing member 110; a water storing member 130 connected to the water collecting member 120 and for storing the collected water; a carbon dioxide collecting member 140 connected to the water collecting member 120 and for collecting carbon dioxide from dry air supplied after the water collecting member 120 collects water; a water electrolysis member 150 for electrolyzing water supplied from the water storing member 130 to generate oxygen and hydrogen; a methanation reaction member 160 for generating a natural gas by methanation reaction of hydrogen supplied from a hydrogen storing member 153 connected to the water electrolysis member 150 and carbon dioxide supplied from a carbon dioxide storing member 141 connected to the carbon dioxide collecting member 140; a separation member 170 having a means for separating the natural gas, carbon dioxide and water contained in a methanation reaction product supplied from the methanation reaction member 160, respectively; a product storing member 180 for storing the natural gas supplied from the separation member 170, from which water and carbon dioxide are removed; and an oxygen storing member 158 for storing oxygen gas supplied from the water electrolysis member 150, wherein an electrical energy required for operating the apparatus is supplied by at least one of a solar cell, regenerated electricity, and idle electricity.

Hereafter, embodiments of the present disclosure will be described in more detail with reference to FIG. 1.

In an embodiment of the present disclosure, air supplied to the air-compressing member 110 is not limited as long as it contains carbon dioxide and water. For example, air in the atmosphere or emissions from various sources (for non-limiting example: emissions from factories, power plants, etc.) may be used as the air. However, the present disclosure may not be limited thereto.

In an embodiment of the present disclosure, the water collecting member 120 may include at least one of a cooling means, an adsorption means and a membrane separation means for collecting water from the compressed air supplied through a compressed-air outlet 111 of the air-compressing member 110.

In an embodiment of the present disclosure, the water collecting member 120 includes a water outlet 121 for supplying the collected water to the water storing member 130 and a dry-air outlet 122 for supplying dry air from which water has been removed to the carbon dioxide collecting member 140.

In an embodiment of the present disclosure, the carbon dioxide collecting member 140 may include at least one of an adsorption means and a membrane separation means for collecting carbon dioxide from the dry air supplied through the dry-air outlet 122 of the water collecting member 120, but may not be limited thereto. Further, the carbon dioxide collecting member 140 may include the carbon dioxide storing member 141 for storing the carbon dioxide collected from the dry air and supplying the carbon dioxide to the methanation reaction member 160. The carbon dioxide storing member 141 may include a means 142 for measuring a flow rate of the carbon dioxide gas supplied to the methanation reaction member 160.

The adsorption means and a membrane separation means provided in the water collecting member 120 and the carbon dioxide collecting member 140 may be formed including at least one molecular sieve material selected from the group consisting of, but not limited to, the following: (i) zeolite; (ii) MFI structured zeolite, ZSM-5, silicalite-1, TS-1 or metallo-silicalite-1; (iii) MEL structured zeolite, ZSM-11, silicalite-2, TS-2 or metallo-silicalite-2; (iv) zeolite A, X, Y, L, beta, mordenite, perialite, ETS-4 or ETS-10; (v) any one of MCM series, SBA series, MSU series or KIT series meso-porous silica; (vi) an organic-inorganic complex meso-pore structured body or laminated material; (vii) an organic zeolite, an organic metal zeolite or coordinate compound zeolite that combines metal ions and ligands in a 3-dimension; (viii) a metal organic framework (MOF) material, a covalent organic framework (COF) material or complexes thereof; (ix) a porous material selected from the group consisting of zeolite, a zeotype-porous molecular sieve, a metal organic framework (MOF) material, a covalent organic framework (COF) material, and complexes thereof.

In an embodiment of the present disclosure, the water electrolysis member 150 may include a proton exchange membrane (PEM) electrolysis means, a solid electrolyte water electrolysis means, or an alkaline electrolysis (AE) means, but may not be limited thereto. The water electrolysis member 150 may decompose the water collected from the compressed air into oxygen and hydrogen using the electrolysis means. The hydrogen generated by electrolysis of the water may be stored in the hydrogen storing member 153 through a hydrogen outlet 151 provided in the water electrolysis member 150 and then supplied into the methanation reaction member 160. The oxygen generated by electrolysis of the water may be supplied to and stored in an oxygen storing member 190 through an oxygen outlet 152 provided in the water electrolysis member 150. The hydrogen storing member 153 may include a means 154 for measuring a flow rate of the hydrogen gas supplied to the methanation reaction member 160.

In an embodiment of the present disclosure, the methanation reaction member 160 may include a thermal reaction means or a plasma reaction means for the methanation reaction, but may not be limited thereto. The methanation reaction member 160 may synthesize a natural gas containing a methane gas as represented by the following methanation reaction formula by a thermal reaction or plasma reaction of hydrogen supplied from the hydrogen storing member 153 connected to the water electrolysis member 150 and carbon dioxide supplied from the carbon dioxide storing member 141 connected to the carbon dioxide collecting member 140:

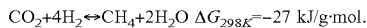

$$CO_2 + 4H_2 \leftrightarrow CH_4 + 2H_2O \quad \Delta G_{298K} = -27 \text{ kJ/g·mol}.$$

The methanation reaction is an exothermic reaction with a reduction in the number of mole. According to Le Chatelier's principle, the reaction is encouraged by increasing the pressure and discouraged by increasing the temperature. The highly exothermic balanced reaction requires good control of the cooling of the cooler in which the reaction takes place. For example, the heat generated during $CO_2$ conversion is about 2.7 kWh during the production of 1 $Nm^3$ of methane. Controlling the temperature inside the reactor, and therefore removing the heat produced by the reaction is one of the keys to minimizing the deactivation of the catalyst by sintering, and maximizing the methane conversion rate.

In an embodiment of the present disclosure, to maximize the production of $CH_4$ by carbon dioxide hydrogenation, $H_2$ and $CO_2$ should have a stoichiometric ratio of about 4:1. For example, to suppress the supply of excessive reactants for the optimized production of $CH_4$, it is desirable to control a $H_2/CO_2$ ratio close to the stoichiometric ratio, i.e., from 3.9 to 4.1. The ratio is a function of a $H_2$ flow rate and a flow rate measurement value of a stoichiometric factor and is controlled by adjusting a $CO_2$ flow rate.

In an embodiment of the present disclosure, the natural gas producing apparatus 100 may include the means 154 for measuring a flow rate of the hydrogen gas supplied to the methanation reaction member 160, the means 142 for measuring a flow rate of the carbon dioxide gas, and a flow rate adjusting means 155 for determining/controlling the flow rate of the carbon dioxide as a function of the measured hydrogen flow rate. The flow rate adjusting means 155 is, for example, an electronic control circuit that multiplies the measured hydrogen flow rate by the determined set point coefficient. The result of the multiplication is delivered to a carbon dioxide flow rate control valve, and the result is identical to a flow rate set point.

In an embodiment of the present disclosure, the methanation reaction member 160 may be used in a pressure range of from about 1 bar to about 100 bar and a predetermined temperature range of from about 230° C. to about 700° C., but may not be limited thereto.

In an embodiment of the present disclosure, the separation member 170 may include: at least one of a distillating separation means, a cooling separation means, a freezing separation means, and a membrane separating means for separating the natural gas, carbon dioxide and water contained in the natural gas product, respectively; a carbon dioxide re-feeding line for re-cycling the separated carbon dioxide to the carbon dioxide collecting member 140; and a water supplying line 173 for supplying the separated water to the water storing member 130, but may not be limited thereto. The separation member 170 may recycle unreacted carbon dioxide through an outlet 172 to the carbon dioxide collecting member 140 connected to a carbon dioxide inlet 143 or recycle the unreacted carbon dioxide to the carbon dioxide storing member 141 (not illustrated) for re-use in the methanation reaction and thus can further improve the carbon dioxide conversion efficiency.

In an embodiment of the present disclosure, the cooling separation means may be configured to cool the natural gas contained in the natural gas product in a temperature range of from about −5° C. to about 60° C., but may not be limited thereto. Almost all of water can be removed from a final natural gas by the cooling separation means.

The separation member 170 may include the water supplying line 173 for supplying the separated water to the water storing member 130 and thus can supply the water to the water electrolysis member 150 or store the water for other uses such as drinking water or agricultural water. A final natural gas product from which water and carbon dioxide have been separated and removed by the separation member 170 may be supplied to the product storing member 180 through a natural gas outlet 171. The final natural gas product from which water and carbon dioxide have been separated and removed may need to undergo additional separation of undesirable compounds such as hydrogen in the downstream of the reactor in order to meet the specifications for injection into a natural gas distribution or transport grid.

In an embodiment of the present disclosure, an electrical energy required for operating the apparatus may be supplied by at least one of a solar cell, regenerated electricity, and idle electricity. However, the present disclosure may not be limited thereto. For example, the regenerated electricity may include electrical energy generated using solar energy, wind power, water power, ocean energy, geothermal energy, bioenergy, and the like, or electrical energy generated using various fuel cells, but my not be limited thereto.

In an embodiment of the present disclosure, the idle electricity may be idle electricity stored using an energy storage system (ESS), but may not be limited thereto. The energy storage system (ESS) is a system that stores surplus electric power from a power plant in a grid and supplies the electric power when electric power is most needed or in case of temporary shortage of electric power to increase the energy efficiency. That is, the ESS refers to a technology of storing a large amount of electric power in various ways, such as by enlarging secondary batteries such as lithium ion batteries or using a flywheel and compressed air energy storage (CAES). Therefore, the ESS is composed of a battery that stores electricity and its relevant devices that efficiently manage the battery.

A second aspect of the present disclosure provides a method for producing a natural gas using carbon dioxide and water in air (FIG. 2), including the following: compressing air using an air-compressing member; collecting water from the compressed air supplied from the air-compressing member to a water collecting member, supplying the water to a water storing member, and supplying dry air from which water has been removed to a carbon dioxide collecting member; collecting carbon dioxide from the dry air in the carbon dioxide collecting member and storing carbon dioxide in a carbon dioxide storing member; supplying water from the water storing member to a water electrolysis member to generate oxygen and hydrogen by electrolysis and storing the generated oxygen and hydrogen in an oxygen storing member and a hydrogen storing member, respectively; and supplying carbon dioxide and hydrogen from each of the carbon dioxide storing member and the hydrogen storing member to a methanation reaction member to generate a natural gas by a methanation reaction, wherein an electric energy required for each of the above steps is supplied by at least one of a solar cell, regenerated electricity and idle electricity.

In an embodiment of the present disclosure, the method for producing a natural gas using carbon dioxide and water in air may further include separating carbon dioxide and water contained in the natural gas product supplied from the methanation reaction member so as to separate the natural gas from which the carbon dioxide and water have been removed, and supplying the separated natural gas to a product storing member, but may not be limited thereto.

In an embodiment of the present disclosure, the method for producing a natural gas using carbon dioxide and water in air may further include recycling the carbon dioxide separated from the natural gas product to the carbon dioxide collecting member, but may not be limited thereto.

Detailed descriptions of the apparatus for producing a natural gas according to the first aspect of the present disclosure may be identically applied to the method for producing a natural gas using carbon dioxide and water in air according to the second aspect of the present disclosure. The redundant descriptions thereof are omitted herein.

A third aspect of the present disclosure provides a natural gas-synthesizing equipment system including the apparatus for producing a natural gas according to the first aspect of the present disclosure and a container including the apparatus.

In an embodiment of the present disclosure, the natural gas-synthesizing equipment system may include at least one of the containers, wherein each member of the apparatus for producing the natural gas is separately contained in each of the at least one container, and the members of the apparatus for producing the natural gas contained in the each container are connected for using the apparatus, but may not be limited thereto.

In an embodiment of the present disclosure, in the natural gas-synthesizing equipment system, each member of the apparatus for producing the natural gas may be miniaturized and may be used for residential use, but may not be limited thereto.

By using the apparatus for producing a natural gas using carbon dioxide and water in air according to the first aspect of the present disclosure, the method for producing a natural gas using carbon dioxide and water in air according to the second aspect of the present disclosure, and the natural gas-synthesizing equipment system according to the third aspect of the present disclosure, a natural gas containing a methane gas can be produced from carbon dioxide and water collected from air using an electric energy such as a solar cell, regenerated electricity and idle electricity. Particularly, in regions, such as deserts, with abundant solar energy but a lack of water, air in the deserts can be compressed to collect and separate water and dry air, hydrogen and oxygen can be generated by electrolysis of the collected water using an electric energy generated by a solar cell or solar power generation with abundant solar energy in the deserts, and carbon dioxide collected from the dry air and the hydrogen can be converted into a natural gas containing methane through a methanation reaction by using the apparatus and method for producing a natural gas according to embodiments of the present disclosure. Also, some of the collected water can be supplied as drinking water, agricultural water, and the like to the desert regions and the oxygen gas can be separately stored and supplied.

EXPLANATION OF REFERENCE NUMERALS

100: Natural gas producing apparatus using carbon dioxide and water in air
110: Air-compressing member
120: Water collecting member
130: Water storing member
140: Carbon dioxide collecting member
141: Carbon dioxide storing member
150: Water electrolysis member
153: Hydrogen storing member 158: Oxygen storing member
160: Methanation reaction member
170: Separation member
180: Product storing member

I claim:

1. An apparatus for producing a natural gas using carbon dioxide and water in air, comprising:
    an air-compressing member;
    a water collecting member for collecting and separating water from the compressed air supplied from the air-compressing member;
    a water storing member connected to the water collecting member and for storing the collected water;
    a carbon dioxide collecting member connected to the water collecting member and for collecting carbon dioxide from dry air supplied after the water collecting member collects water;
    a water electrolysis member for electrolyzing water supplied from the water storing member to generate oxygen and hydrogen;
    a methanation reaction member for generating a natural gas by methanation reaction of hydrogen supplied from a hydrogen storing member connected to the water electrolysis member and carbon dioxide supplied from a carbon dioxide storing member connected to the carbon dioxide collecting member;
    a separation member having a means for separating the natural gas, carbon dioxide and water contained in a methanation reaction product supplied from the methanation reaction member, respectively;
    a product storing member for storing the natural gas supplied from the separation member, from which water and carbon dioxide are removed; and
    an oxygen storing member for storing oxygen gas supplied from the water electrolysis member,
    wherein an electrical energy required for operating the apparatus is supplied by at least one of a solar cell, regenerated electricity, and idle electricity.

2. The apparatus for producing natural gas using carbon dioxide and water in air of claim 1, further comprising:
    a means for measuring a flow rate of the hydrogen gas supplied to the methanation reaction member, a means for measuring a flow rate of the carbon dioxide gas, and a flow rate adjusting means for determining/controlling the flow rate of the carbon dioxide as a function of the measured hydrogen flow rate.

3. The apparatus for producing natural gas using carbon dioxide and water in air of claim 1, wherein the water collecting member includes at least one of a cooling means, an adsorption means and a membrane separation means for collecting water from the compressed air.

4. The apparatus for producing natural gas using carbon dioxide and water in air of claim 1, wherein the carbon dioxide collecting member includes at least one of an adsorption means and a membrane separation means for collecting carbon dioxide from the dry air.

5. The apparatus for producing natural gas using carbon dioxide and water in air of claim 1, wherein the water electrolysis member includes a proton exchange membrane (PEM) electrolysis means, a solid electrolyte water electrolysis means, or an alkaline electrolysis means.

6. The apparatus for producing natural gas using carbon dioxide and water in air of claim 1, wherein the methanation reaction member includes a thermal reaction means or a plasma reaction means for the methanation reaction.

7. The apparatus for producing natural gas using carbon dioxide and water in air of claim 1, wherein the separation member includes:
    at least one of a distillating separation means, a cooling separation means, a freezing separation means, and a membrane separating means for separating the natural gas, carbon dioxide and water contained in the natural gas product, respectively;
    a carbon dioxide re-feeding line for re-cycling the separated carbon dioxide to the carbon dioxide collecting member; and
    a water supplying line for supplying the separated water to the water storing member.

8. The apparatus for producing natural gas using carbon dioxide and water in air of claim 7, wherein the natural gas contained in the natural gas product is separated by cooling the natural gas in a temperature range of from −5° C. to 60° C.

9. A method for producing a natural gas using carbon dioxide and water in air using the apparatus of claim 1, comprising:
    compressing air using the air-compressing member;
    collecting water from the compressed air supplied from the air-compressing member to the water collecting member, supplying the water to the water storing member, and supplying dry air from which water has been removed to the carbon dioxide collecting member;
    collecting carbon dioxide from the dry air in the carbon dioxide collecting member and storing carbon dioxide in the carbon dioxide storing member;
    supplying water from the water storing member to the water electrolysis member to generate oxygen and hydrogen by electrolysis and storing the generated oxygen and hydrogen in the oxygen storing member and the hydrogen storing member, respectively; and
    supplying carbon dioxide and hydrogen from each of the carbon dioxide storing member and the hydrogen storing member to the methanation reaction member to generate the natural gas by the methanation reaction,
    wherein an electric energy required for each of the above steps is supplied by the at least one of the solar cell, the regenerated electricity, and the idle electricity.

10. The method for producing natural gas using carbon dioxide and water in air of claim 9, further comprising:
    separating carbon dioxide and water contained in the natural gas product supplied from the methanation reaction member so as to separate the natural gas from which the carbon dioxide and water have been removed, and supplying the separated natural gas to the product storing member.

11. The method for producing natural gas using carbon dioxide and water in air of claim 10, further comprising:
    recycling the carbon dioxide separated from the natural gas product to the carbon dioxide collecting member or the carbon dioxide storing member.

12. A natural gas-synthesizing equipment system, comprising:
    the apparatus for producing a natural gas of claim 1 and a container comprising the apparatus.

13. The natural gas-synthesizing equipment system of claim 12, further comprising:
    at least one of the containers, wherein each member of the apparatus for producing the natural gas is separately contained in each of the at least one container, and the members of the apparatus for producing the natural gas contained in the each container are connected for using the apparatus.

14. The natural gas synthesis equipment system of claim 12, wherein each member of the apparatus for producing the natural gas is miniaturized and may be used for residential use.

* * * * *